(12) United States Patent
Bhavaraju et al.

(10) Patent No.: US 8,382,974 B2
(45) Date of Patent: Feb. 26, 2013

(54) SENSOR TO MEASURE A CONCENTRATION OF ALKALI ALCOHOLATE

(75) Inventors: Sai Bhavaraju, West Jordan, UT (US); Shekar Balagopal, Sandy, UT (US); Justin Pendelton, Salt Lake City, UT (US); Peter Wall, Provo, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 495 days.

(21) Appl. No.: 12/706,125

(22) Filed: Feb. 16, 2010

(65) Prior Publication Data

US 2011/0042238 A1 Feb. 24, 2011

Related U.S. Application Data

(60) Provisional application No. 61/234,957, filed on Aug. 18, 2009.

(51) Int. Cl.
*G01N 27/26* (2006.01)
(52) U.S. Cl. ............... 205/781.5; 422/82.01; 422/68.1; 204/415
(58) Field of Classification Search ............ 204/252, 204/435, 400, 415, 406; 205/789, 781.5; 422/68.1, 82.01
See application file for complete search history.

(56) References Cited

U.S. PATENT DOCUMENTS

| | | | | |
|---|---|---|---|---|
| 4,227,973 A | * | 10/1980 | Ruzicka et al. | 205/781 |
| 4,513,280 A | * | 4/1985 | Hannan et al. | 205/778 |
| 4,686,012 A | | 8/1987 | Engell et al. | |
| 4,814,062 A | | 3/1989 | Redey et al. | |
| 5,120,422 A | | 6/1992 | Liu et al. | |
| 6,913,930 B2 | * | 7/2005 | Bevan et al. | 436/163 |
| 2003/0201159 A1 | * | 10/2003 | Kuriyama et al. | 204/157.15 |
| 2005/0177008 A1 | * | 8/2005 | Balagopal et al. | 568/851 |
| 2005/0178185 A1 | * | 8/2005 | Negri | 73/23.34 |
| 2006/0169594 A1 | | 8/2006 | Balagopal et al. | |
| 2006/0249386 A1 | * | 11/2006 | Bower et al. | 204/433 |
| 2008/0000771 A1 | * | 1/2008 | Kakiuchi et al. | 204/435 |
| 2008/0293997 A1 | * | 11/2008 | Buhlmann et al. | 600/17 |

OTHER PUBLICATIONS

Khireddine et al. (Sensors and Actuators B 40 (1997) 223-230).*
Heyrovsk (Electroanalysis 18, 2006, No. 2, 121-126).*
Choi, Sok Jin "International Search Report", App. No. PCT/US2010/042940, (Feb. 8, 2011), 1-3.
Choi, Sok Jin "Written Opinion of the International Searching Authority", App. No. PCT/US2010/042940, (Feb. 8, 2011),1-3.

* cited by examiner

*Primary Examiner* — J. Christopher Ball
*Assistant Examiner* — Jennifer Dieterle
(74) *Attorney, Agent, or Firm* — David Fonda

(57) ABSTRACT

A sodium sensor to measure a concentration of sodium methylate in methanol. The sensor assembly includes a solid alkali ion conducting membrane, a reference electrode, and a measurement electrode. The solid alkali ion conducting membrane transports ions between two alkali-containing solutions, including an aqueous solution and a non-aqueous solution. The reference electrode is at least partially within an alkali halide solution of a known alkali concentration on a first side of the solid alkali ion conducting membrane. The measurement electrode is on a second side of the solid alkali ion conducting membrane. The measurement electrode exhibits a measurable electrical characteristic corresponding to a measured alkali concentration within the non-aqueous solution, to which the measurement electrode is exposed.

9 Claims, 9 Drawing Sheets

SENSOR TO MEASURE A CONCENTRATION OF ALKALI ALCOHOLATE

CROSS-REFERENCE TO RELATED APPLICATIONS

This application claims the benefit of priority of U.S. Provisional Application No. 61/234,957, entitled "Sensor to Measure a Concentration of Alkali Alcoholate," filed on Aug. 18, 2009 and incorporated herein by this reference.

BACKGROUND

Biodiesel is an alternative fuel source to petrodiesel, JP-8, and standard gasoline. The use of biodiesel is growing in popularity and market penetration in the United States and worldwide. In general, biodiesel may be defined as a petrodiesel equivalent processed fuel derived from biological sources. Typically, biodiesel is a fuel produced from mono-alkyl esters of long chain fatty acids derived from triglycerides. A "mono-alkyl ester" is the product of the reaction of a straight chain alcohol (e.g., methanol or ethanol) with a triglyceride to form glycerine (also known as glycerin or glycerol) and the esters of long chain fatty acids. The triglycerides are commonly obtained from vegetable oils and animal fats of various origins. Biodiesel has a general formula R'OOCR, where R' is a straight chain lower alkyl (e.g., $C_1$ to $C_8$) and R is a hydrocarbon chain from C8 to C24.

One method of making biodiesel involves the reaction of triglycerides with methanol and with an alkali alcoholate catalyst. Electrolytic systems have been proposed for use in producing alkali alcoholates from alkali salt and alkali hydroxide solutions. In one example, a sodium-based process is used to make sodium methylate from sodium metal as a raw material. In another example, sodium methylate is made from a sodium amalgam produced from the chlor-alkali electrolysis in a mercury cell by reacting amalgam with alcohol.

Regardless of how the alkali alcoholate is produced, it can be important to measure the concentration of alkali alcoholate product in order to properly control the process for making biodiesel fuel. Although some conventional alkali ion sensors exist, the conventional alkali ion sensors are designed to function based on aqueous electrochemistry. Unfortunately, these conventional alkali ion sensors will not operate correctly with non-aqueous solutions because the aqueous solution present in the reference electrode of the conventional alkali ion sensor mixes with the non-aqueous solution, which changes the reference electrode potential of the conventional alkali ion sensor.

SUMMARY

Embodiments of an apparatus are described. In one embodiment, the apparatus is a sensor assembly for measurement of an alkali compound in a non-aqueous solution. The sensor assembly includes a solid alkali ion conducting membrane, a reference electrode, and a measurement electrode. The solid alkali ion conducting membrane transports ions between two alkali-ion-containing solutions, including an aqueous solution and a non-aqueous solution. The reference electrode is at least partially within an alkali salt aqueous solution of a known alkali concentration on a first side of the solid alkali ion conducting membrane. The measurement electrode is on a second side of the solid alkali ion conducting membrane. The measurement electrode exhibits a measurable electrical characteristic corresponding to a measured alkali alcoholate concentration within the non-aqueous solution, to which the measurement electrode is exposed.

In another embodiment, the reference electrode is in contact with an alkali salt in a saturated aqueous solution. The measurement electrode is provided to measure an alkali alcoholate in a non-aqueous solution. The solid alkali ion conducting membrane is interposed between the reference and measurement electrodes to prevent mixing of the aqueous and non-aqueous solutions and for transporting alkali ions from one electrode to another. An Open Circuit Voltage (OCV) is established due to the potential difference between the measurement electrode immersed in alkali alcoholate solution and the reference electrode immersed in saturated aqueous solution. The open circuit voltage is indicative of a concentration of the alkali alcoholate in the non-aqueous solution as the reference electrode potential is constant. Other embodiments are also described. For example, the sensor assembly may generate a current, rather than a voltage, as the measurable electrical characteristic used to determine the concentration of the alkali alcoholate in the non-aqueous solution.

Embodiments of a system are also described. In one embodiment, the system is a sensor system for measurement of a non-aqueous compound. In an embodiment, the sensor system includes a sensor and a testing module. The sensor includes a first fluid chamber, a reference electrode, a measurement electrode, and a solid alkali ion conducting membrane. The first fluid chamber contains an alkali-based aqueous solution. The reference electrode is at least partially in contact with the alkali-based aqueous solution in the first fluid chamber. The measurement electrode is provided for contact with an alkali-based non-aqueous solution. The solid alkali ion conducting membrane separates the measurement electrode from the reference electrode and the alkali-based aqueous solution. The solid alkali ion conducting membrane allows alkali ions to transfer between the aqueous and non-aqueous solutions. The testing module is coupled to the sensor. The testing module measures a concentration of an alkali alcoholate in the non-aqueous solution based on a measurable electrical characteristic exhibited by at least one of the measurement and reference electrodes. Other embodiments of the sensor system are also described.

Embodiments of a method are also described. In one embodiment, the method is a method for measuring a concentration of an alkali-based compound within a non-aqueous solution. The method includes exposing a reference electrode to an alkali halide in an aqueous solution of a known alkali concentration. The method also includes exposing a measurement electrode to an alkali alcoholate in a non-aqueous solution. The method also includes exchanging alkali ions between the aqueous and non-aqueous solutions via a solid alkali ion conducting membrane. The method also includes measuring an electrical characteristic of at least one of the reference and measurement electrodes. The electrical characteristic is dependent on the concentration of the alkali alcoholate in the non-aqueous solution. The method also includes determining the concentration of the alkali alcoholate in the non-aqueous solution from the measured electrical characteristic. Other embodiments of the method are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1A:
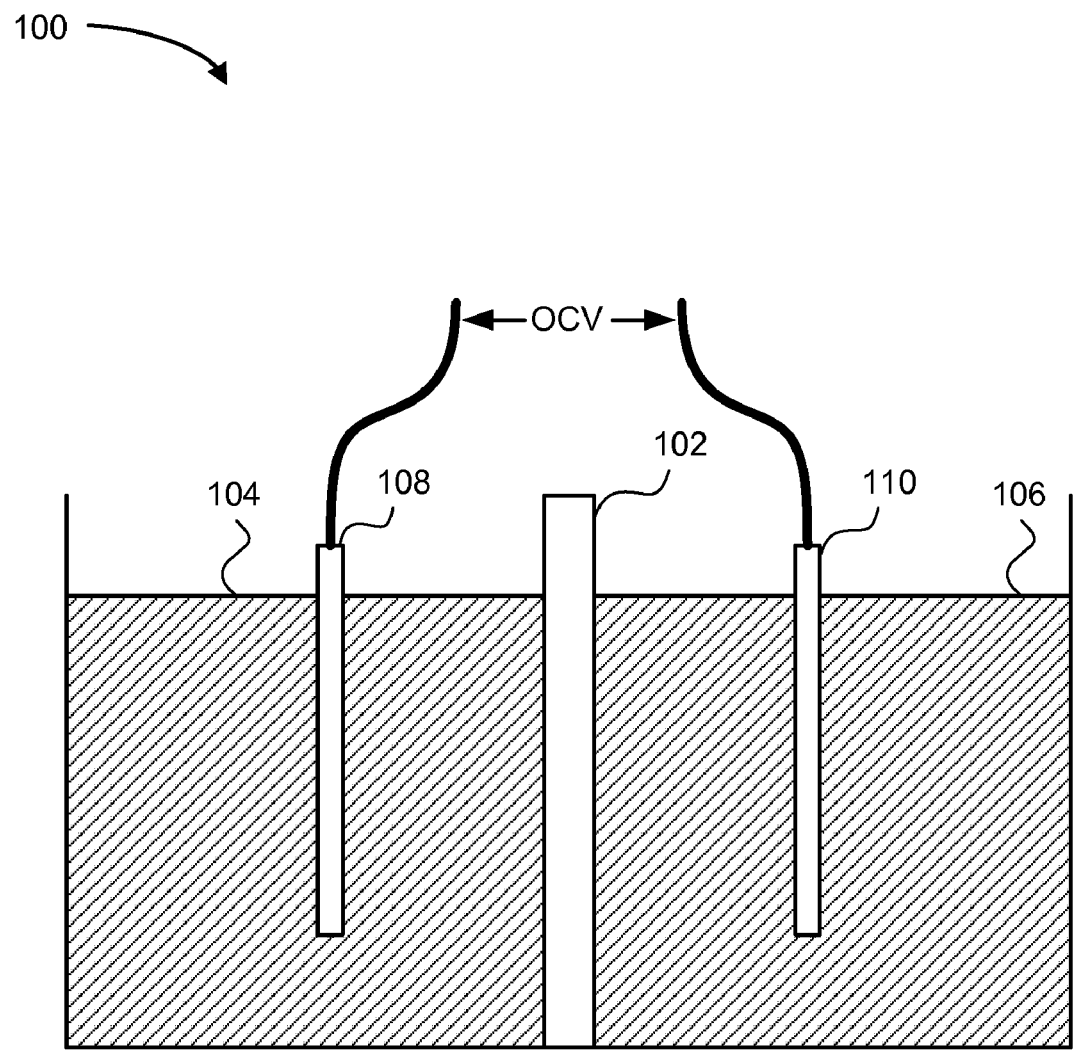
FIG. 1A depicts a schematic diagram of one embodiment of a sensor assembly for use in measuring a concentration of alkali alcoholate in a non-aqueous solution.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated. Attachment A is also made part of this description and sets forth various embodiments, and is incorporated herein by this reference.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments of are described herein, at least some of the described embodiments include a sensor to detect a concentration of an alkali compound within a non-aqueous solution. Some examples of non-aqueous solutions that may be used in embodiments of the sensor include ethanol, methanol, higher aliphatic alcohols, and other common organic solvents. The sensor includes a solid alkali ion conducting membrane that allows alkali ions to transfer between the non-aqueous solution and an aqueous solution, without mixing the aqueous and non-aqueous solutions. Electrodes exposed to the aqueous and non-aqueous solutions exhibit a measurable electrical characteristic such as an open circuit voltage or a current. As a specific example, the aqueous solution may be a saturated sodium chloride (NaCl) solution, and the non-aqueous solution may be a methanol ($CH_3OH$) with sodium methylate ($NaOCH_3$). By measuring the concentration of sodium methylate in the methanol, producers of biodiesel can control the production process more carefully. Other embodiment may use other alkali ion conducting aqueous solutions (e.g. sodium, lithium or potassium carbonates, sulfates, hydroxides) and non-aqueous solutions (e.g. sodium, lithium or potassium carboxylates in methanol solvent).

FIG. 1A depicts a schematic diagram of one embodiment of a concentration sensor assembly 100 for use in measuring a concentration of alkali alcoholate in a non-aqueous solution 104. The illustrated sensor assembly 100 includes a solid alkali ion conducting membrane 102, the non-aqueous solution 104, an aqueous solution 106, a measurement electrode 108, and a reference electrode 110. Although the sensor assembly 100 is shown and described with certain components and functionality, other embodiments of the sensor assembly may include fewer or more components to implement less or more functionality.

For convenience, embodiments of the solid alkali ion conducting membrane 102 are described herein as a solid alkali sodium ion conducting membrane. Similarly, the non-aqueous and aqueous solutions 104 and 106 are described herein as sodium-based solutions. In a specific example, the non-aqueous solution 104 is methanol ($CH_3OH$) which includes sodium methylate ($NaOCH_3$), and the aqueous solution 106 is a saturated solution of sodium chloride (NaCl). However, other embodiments may use other types of solid alkali ion conducting membranes and/or solutions.

Figure 1B:
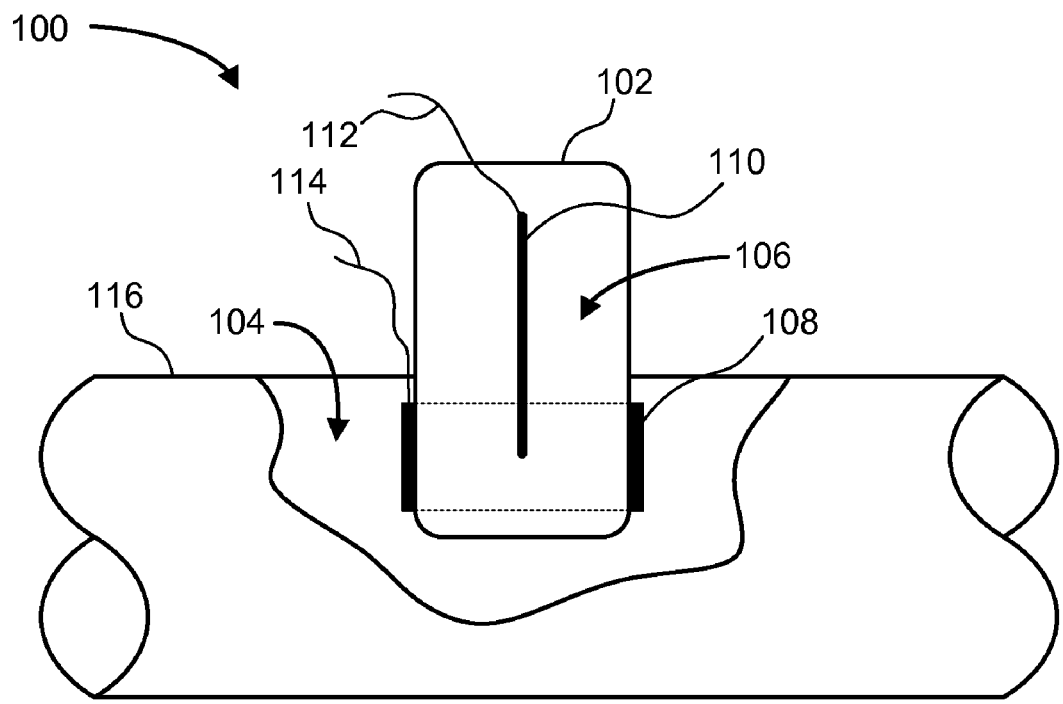
FIG. 1B depicts one specific example of the sensor assembly of FIG. 1A.
Figure 1C:
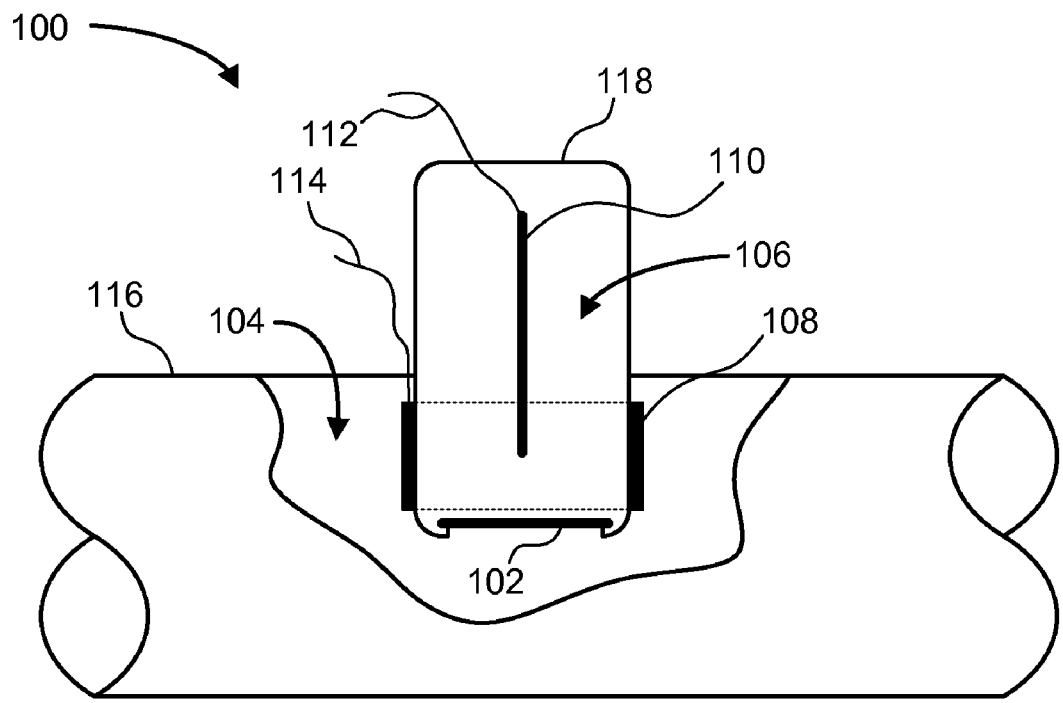
FIG. 1C depicts another specific example of the sensor assembly of FIG. 1A.

In one embodiment, the solid alkali sodium ion conducting membrane 102 is a sodium cation conducting membrane. One example of a sodium cation conducting membrane is a ceramic sodium membrane such as a sodium super-ionic conductor (NaSICON). In another embodiment, the sodium cation conducting membrane is a sodium-Nafion (Na-Nafion) membrane. In another embodiment, the sodium cation conducting membrane is a sodium-based glass membrane. In yet another embodiment the cation conducting membrane is a composite ceramic and polymer membrane. Other embodiments may use other types of sodium (or other alkali-based) membranes. Specific examples of the solid alkali sodium ion conducting membrane are shown in FIGS. 1B and 1C and described in more detail below.

In general, the cation conducting membrane is capable of selectively transporting specific cations (e.g., $Na^+$) between solutions on either side of the cation conducting membrane. Some non-limiting examples of cation conducting membranes that are suitable for use with embodiments described herein include any known or novel type of NaSICON membrane (including, but not limited to NaSICON-type membranes produced by Ceramatec Inc. of Salt Lake City, Utah), lithium super-ionic conductor (LiSICON) membranes, potassium super-ionic conductor (KSICON) membranes, and other polymeric cation conducting membranes (such as NAFION® membranes produced by DuPont). For convenience, general references to MSICON membranes may be used to collectively or generically refer to a membrane that is capable of selectively transporting M ions, where M is lithium, sodium, and/or potassium. More generally, in some embodiments, the cation conducting membrane can be any material with minimal sodium conductivity. Also, the cation conducting membrane may be a porous or dense solid material. The cation ion membrane can be a planar or tubular configuration of a dense NaSICON membrane.

The first solution 104, in some embodiments, is a material containing sodium. For example, the first solution 104 may be methanol containing a certain percent sodium methylate. The second solution 106 is separated from the first solution 104 by the solid alkali ion conducting membrane 102. In some embodiments, the second solution 106 acts as an electrical potential reference relative to the first solution 104.

As explained above, the non-aqueous and aqueous solutions 104 and 106 are both alkali-containing solutions. In a specific embodiment, the non-aqueous solution 104 is methanol ($CH_3OH$) which includes sodium methylate ($NaOCH_3$), and the aqueous solution 106 is a saturated solution of sodium chloride (NaCl). The non-aqueous and aqueous solutions 104 and 106 are separated by the sodium solid alkali ion conducting membrane 102, which prevents the solutions 104 and 106 from mixing together. Hence, the sodium solid alkali ion conducting membrane 102 prevents the non-aqueous solution 104 from mixing with the aqueous solution 106, even though the sodium solid alkali ion conducting membrane 102 allows sodium ions to transport between the two sodium-based solutions 104 and 106.

The measurement electrode 108 is located at least partially in contact with the non-aqueous solution 104. The specific geometrical shape and size of the measurement electrode 108 depends on the type of chamber or location in which the non-aqueous solution 104 is contained. In some embodiments, the measurement electrode 108 is a rod that is exposed within a flow or volume of the non-aqueous solution 104. In one embodiment, the rod may be solid cylindrically shaped. In other embodiments, the measurement electrode 108 is a disc that has one surface exposed to the non-aqueous solution 104. In some embodiments, the disc-shaped measurement electrode 108 allows the non-aqueous solution 104 to flow past the measurement electrode 108 without interruption of the flow. In another embodiment, the measurement electrode 108 is a coating on a substrate. For example, the measurement electrode 108 may be a conductive material (e.g., Pt) applied to the outer surface of a tube (e.g., see FIG. 1C) which extends at least partially within the non-aqueous solution 104.

Also, the measurement electrode 108 is made of or includes a material that is chemically inert in the presence of the non-aqueous solution 104. For example, the measurement electrode 108 may be formed of platinum (Pt), gold (Au) or silver (Ag) that are chemically inert in the presence of sodium methylate ($NaOCH_3$). In another embodiment, the measurement electrode 108 is formed of a composition of materials which resist corrosion in the presence of the non-aqueous solution 104. For example, the measurement electrode 108 may have a coating that is chemically inert in the presence of the non-aqueous solution 104.

Similar to the measurement electrode 108, the reference electrode 110 is located at least partially in contact with the aqueous solution 106. The shape of the reference electrode 110 may depend on the shape of the chamber in which the aqueous solution is contained. In one embodiment, a fixed volume of the aqueous solution 106 is contained in an enclosed chamber. Depending on the construction of the sensor and geometrical considerations, the internal aqueous solution volume could be as low as 1 ml to up to 25 ml or even 50 ml. The reference electrode 110 extends into the enclosed chamber for exposure to the aqueous solution 106. In one embodiment, in which the aqueous solution 106 includes sodium chloride, the reference electrode 110 is made of a silver-silver-chloride (Ag/AgCl) material. Other embodiments may use other materials for the reference electrode 106. Some examples of other materials include Calomel, $Hg/HgO$, $Hg/Hg_2SO_4$, and so forth.

Using the setup described herein, or another similar setup, an electrical parameter may be measured at one or both of the electrodes 108 and 110 in order to determine a concentration of the sodium methylate (or other alkali alcoholate) within the non-aqueous solution. The concentration is determined based on stable electrical characteristics of the electrodes 108 and 110 over time. In the depicted embodiment, a potentiometer is used to measure an open circuit voltage (OCV, i.e., potential difference) between the electrodes 108 and 110. The measured OCV between the measurement and reference electrodes 108 and 110 should be high enough to measure above typical noise levels. In another embodiment, an ammeter is used to measure a current between the electrodes 108 and 110.

FIG. 1B depicts one specific example of the sensor assembly 100 of FIG. 1A. In the illustrated embodiment, the solid alkali ion conducting membrane 102 is formed as a cylindrical tube of NaSICON which encloses the aqueous solution 106 and the reference electrode 110. Although shown as a cylindrical tube, other embodiments may use a different shape of enclosure for the solid alkali ion conducting membrane 102. Also, although described as a NaSICON tube, other embodiments may use a different material, as described above. A conductive wire 112 connects the reference electrode 110 to electronic circuitry (see FIG. 2) which evaluates the signals from the reference electrode 110. The measurement electrode 108 is placed on or applied to the outer surface of the NaSICON tube, and another conductive wire 114 connects the measurement electrode 108

The measurement electrode 108 and the corresponding portion of the NaSICON tube are inserted into a container 116 of the non-aqueous solution 104. In the illustrated embodiment, the container 116 is shown as a portion of tubing (with a cut-away section to see the sensor assembly 100) used to direct a flow of the non-aqueous solution 104. However, in other embodiments, the sensor assembly 100 may be mounted within a different type of container which includes a non-aqueous solution.

FIG. 1C depicts another specific example of the sensor assembly 100 of FIG. 1A. Although similar in many aspects to the sensor assembly 100 of FIG. 1B, the sensor assembly 100 of FIG. 1C includes a disc-shaped solid alkali ion conducting membrane 102 that is mounted at an end of the cylindrical tube 118. In this embodiment, the cylindrical tube 118 may be formed of a material other than NaSICON or another ion conducting membrane. A surface of the disc-shaped solid alkali ion conducting membrane 102 is exposed to the non-aqueous solution 104 within the container 116. Other embodiments may implement other shapes and/or configurations of solid alkali ion conducting membranes 102, enclosures 116 and 118, and electrodes 108 and 110.

Figure 2:
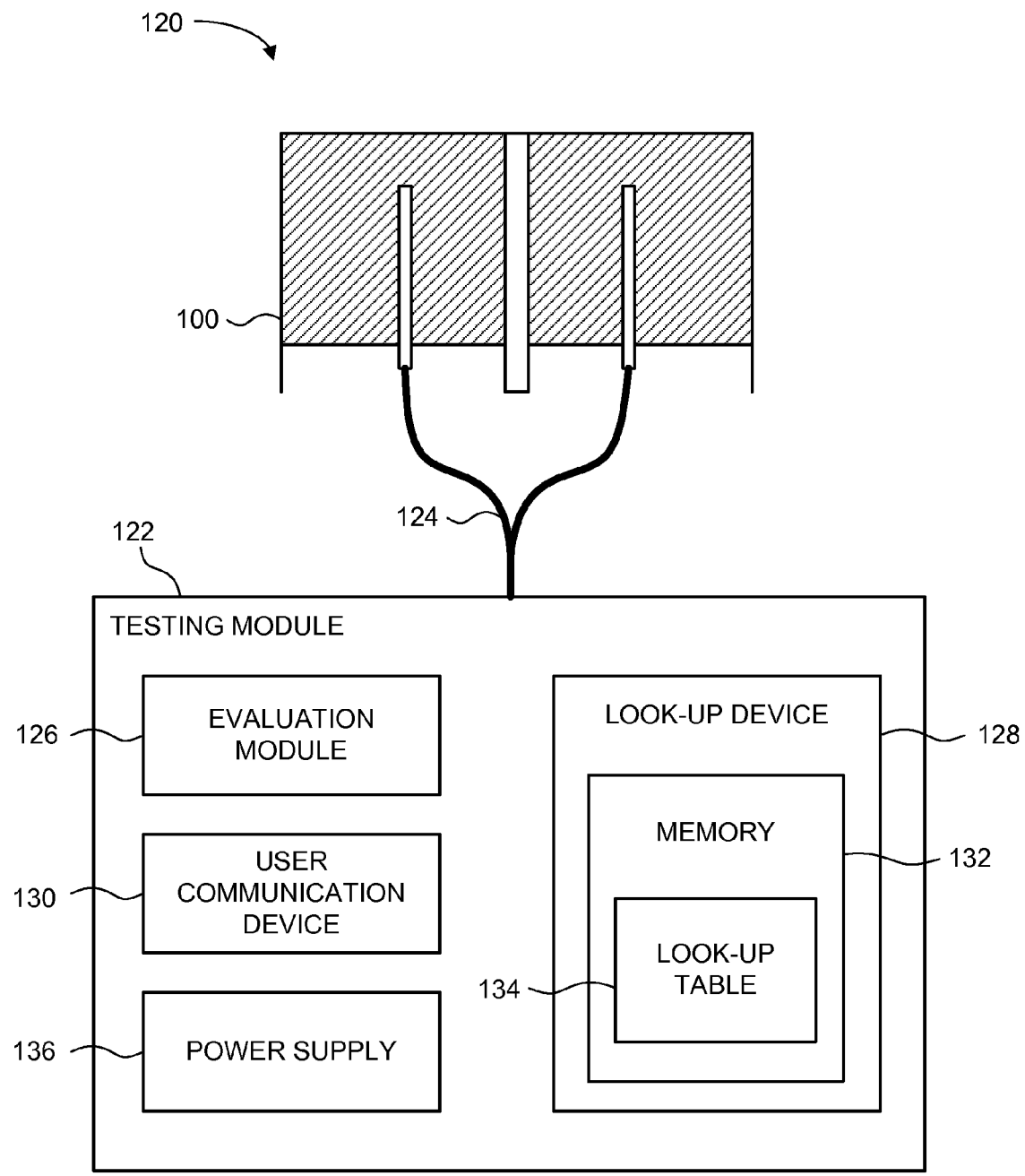
FIG. 2 depicts a schematic block diagram of one embodiment of a sensor system which includes the sensor assembly of FIG. 1A.

In some embodiments, the physical structure of the sensor assembly 100 is manufactured and/or assembled to tolerate high flow rates and pressures. In further embodiments, the sensor assembly 100 has a physical structure that is substantially explosion-resistant. FIG. 2 depicts a schematic block diagram of one embodiment of a sensor system 120 which includes the sensor assembly 100 of FIG. 1A. In the illustrated embodiment, the sensor assembly 100 is connected to a testing module 122 via electrical leads 124. In general, the testing module 122 determines a concentration of the sodium methylate in the non-aqueous solution 104 based on the electrical parameter(s) obtained via the electrical leads 124. Although the sensor system 120 is shown and described with certain components and functionality, other embodiments of the sensor system may include fewer or more components to implement less or more functionality. In one embodiment, the sensor system 120 is configured to operate at a temperature ranging between about −10° C. and about 66° C. The sensor system 120 is also configured to measure the concentration of sodium methylate under flow conditions exceeding 250 psi pressure differential.

The depicted testing module 122 includes an evaluation module 126, a look-up device 128, a user communication device 130, and a power supply 136. Other embodiment may include further components. For example, some embodiments of the testing module 122 include a temperature compensation device to measure a temperature of the sensor assembly 100 and/or the non-aqueous solution 104 and to compensate for the temperature fluctuations. One example of a temperature compensation device includes a resistive thermocouple device (RTD), although other embodiments may use other types of temperature compensation devices. Other embodiments of the testing module 122 include, but are not limited to, a signal amplifier, a filter, a signal output, a sampling analog-to-digital converter (ADC), and so forth. Furthermore, in some embodiments, the testing module 122 may be implemented as a standalone device that is located at or near the site of the sensor assembly 100.

In one embodiment, the evaluation module 126 compares electrical potential readings from the electrodes 108 and 110 of the sensor assembly 100 and evaluates the potential difference between the electrodes 108 and 110 to determine the concentration of the sodium methylate in the non-aqueous solution 104. In another embodiment, the evaluation module 126 measures amperage between both of the electrodes 108 and 110 of the sensor assembly 100 and evaluates the measured current to determine the concentration of the sodium methylate in the non-aqueous solution 104.

In one embodiment, the evaluation module 126 transmits data corresponding to the measured electrical characteristic to the look-up device 128. The look-up device 128 includes an electronic memory device 132. The memory 132 stores a look-up table 134, or another data structure, which can be used to find a concentration value based on the measured electrical characteristic. In one embodiment, the look-up table 134 is indexed by values or ranges for the measured electrical characteristic, which corresponds to a percentage or other concentration value of the sodium methylate in the non-aqueous solution 104. Alternatively, the memory 132 may include an algorithm which computes a concentration value of the sodium methylate in the methanol based on the measured electrical characteristic.

The look-up device 128 obtains the concentration value corresponding to the measured electrical characteristic and transmits the obtained concentration value to the user communication device 130. The user communication device 130 communicates the data to a user. For example, the user communication device 130 may be any type of visual and/or audible communication device capable of conveying a quantitative and/or qualitative indication of the sodium methylate concentration to a user. In one embodiment, the user communication device 130 includes a readout screen that generates a visual depiction of the concentration value. In another embodiment, the user communication device 130 includes a light or other visual indicator that illuminates or is triggered upon realizing a predetermined concentration value or range. For example, the light may illuminate upon measuring the sodium methylate at about 10-12 weight percent (wt %) of the non-aqueous solution 104. In other embodiments, the visual and/or audible indication may be triggered as an alarm if the concentration value is different from the predetermined concentration value or outside of a predetermined concentration range. Other embodiments of the user communication device 130 employ another form of communication to communicate information to the user.

Figure 3A:
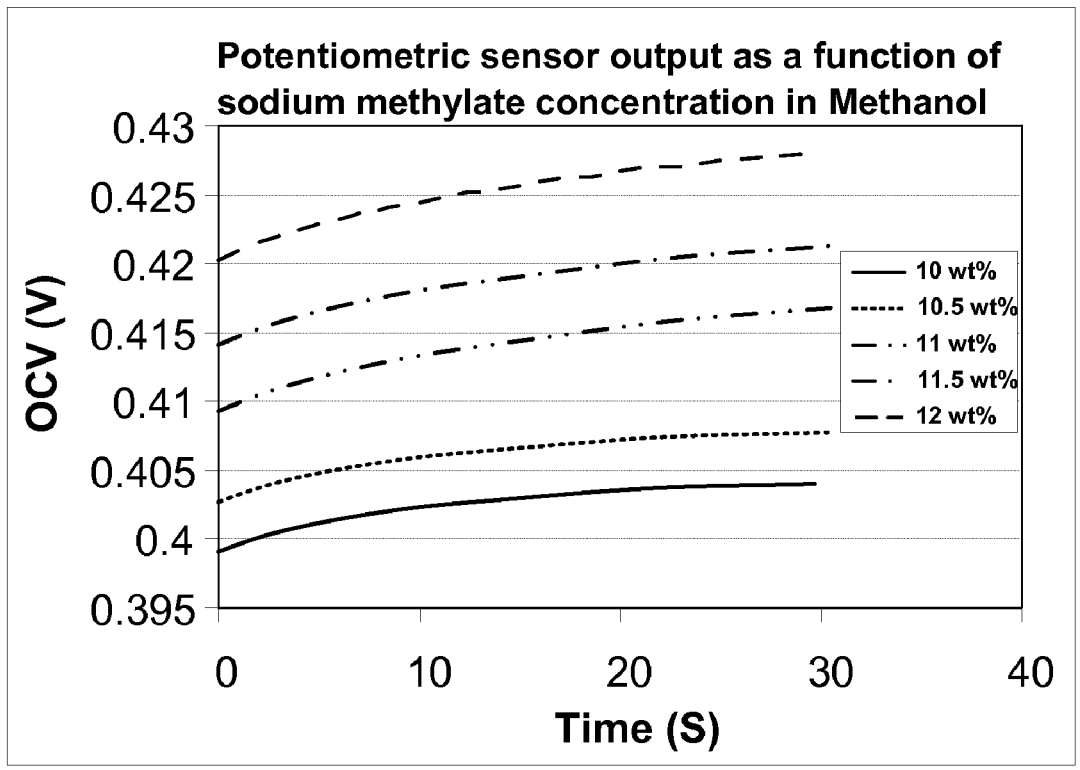
FIG. 3A depicts a graph of several examples of sensor outputs as a function of sodium methylate concentration in methanol.

FIG. 3A depicts a graph of several examples of sensor outputs as a function of sodium methylate concentration in methanol. These measurements were made in stagnant sodium methylate solutions. In the illustrated examples, the sensor outputs are potentiometric sensor outputs, so the values are shown as open circuit voltages (OCV). The OCV for each concentration (expressed as a wt %) of sodium methylate varies over time with a gradual increase of less than 0.01 V over 30 s. The OCV signal can be seen to have stabilized after 30 seconds. Specifically, the OCV for a solution of 10.0 wt % concentration varies between about 0.42-0.428 V. The OCV for a solution of 10.5 wt % concentration varies between about 0.414-0.421 V. The OCV for a solution of 11.0 wt % concentration varies between about 0.409-0.417 V. The OCV for a solution of 11.5 wt % concentration varies between about 0.403-0.408 V. The OCV for a solution of 12.0 wt % concentration varies between about 0.399-0.404 V. Using this data, embodiments of the sensor assembly 100 and the sensor system 120 are capable of detecting the concentration level of the sodium methylate with an accuracy of at least 0.05 wt %. Other embodiments may be implemented with minor modifications in order to achieve a higher accuracy and/or more stability in a shorter amount of time.

Figure 3B:
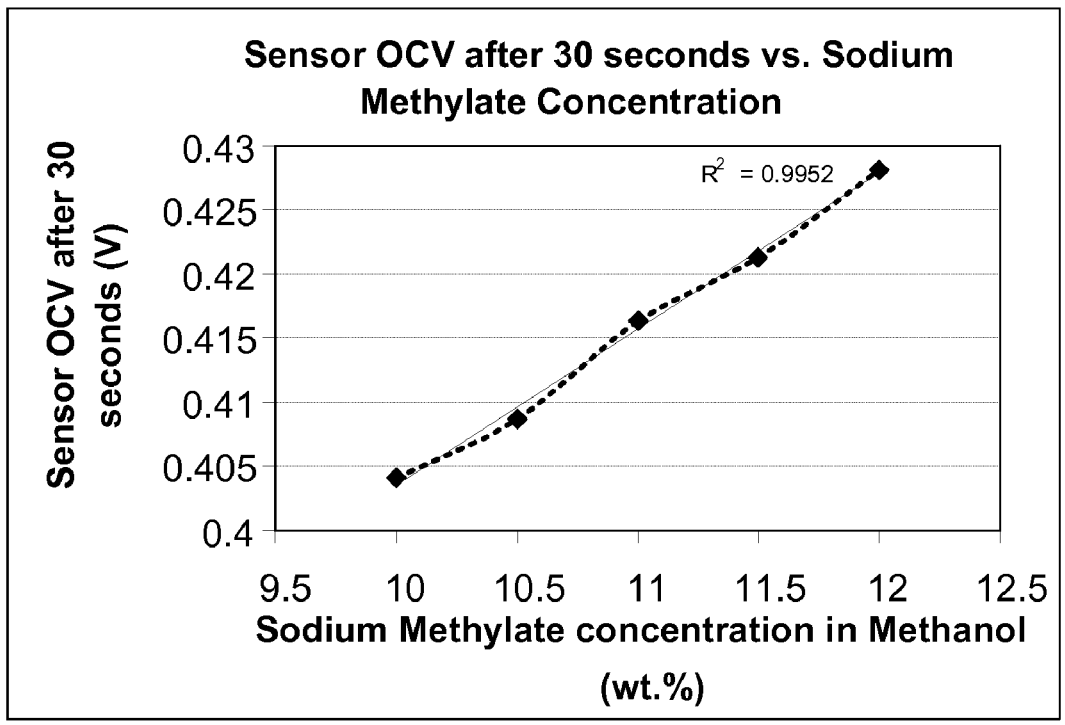
FIG. 3B depicts a graph of one example of a stable open circuit voltage of the sensor assembly of FIG. 1A as a function of sodium methylate concentration in methanol.

FIG. 3B depicts a graph of one example of a stable open circuit voltage of the sensor assembly 100 as a function of sodium methylate concentration in methanol. For reference, the Open Circuit Voltage (OCV) values shown in FIG. 3B approximately correspond to the OCV values shown in FIG. 3A at 30 s. As depicted, the OCV response of the sensor assembly 100 is approximately linear with respect to the concentration of sodium methylate in the methanol. Therefore, a sensor reading can be evaluated and aligned with a specific concentration value from a look-up table 134 to determine a concentration value for the sodium methylate in the non-aqueous solution 104. In another embodiment, the sensor reading can be used to compute a specific concentration value based on an algorithm or mathematical expression which describes the known relationship between the OCV and the concentration values.

Figure 4:
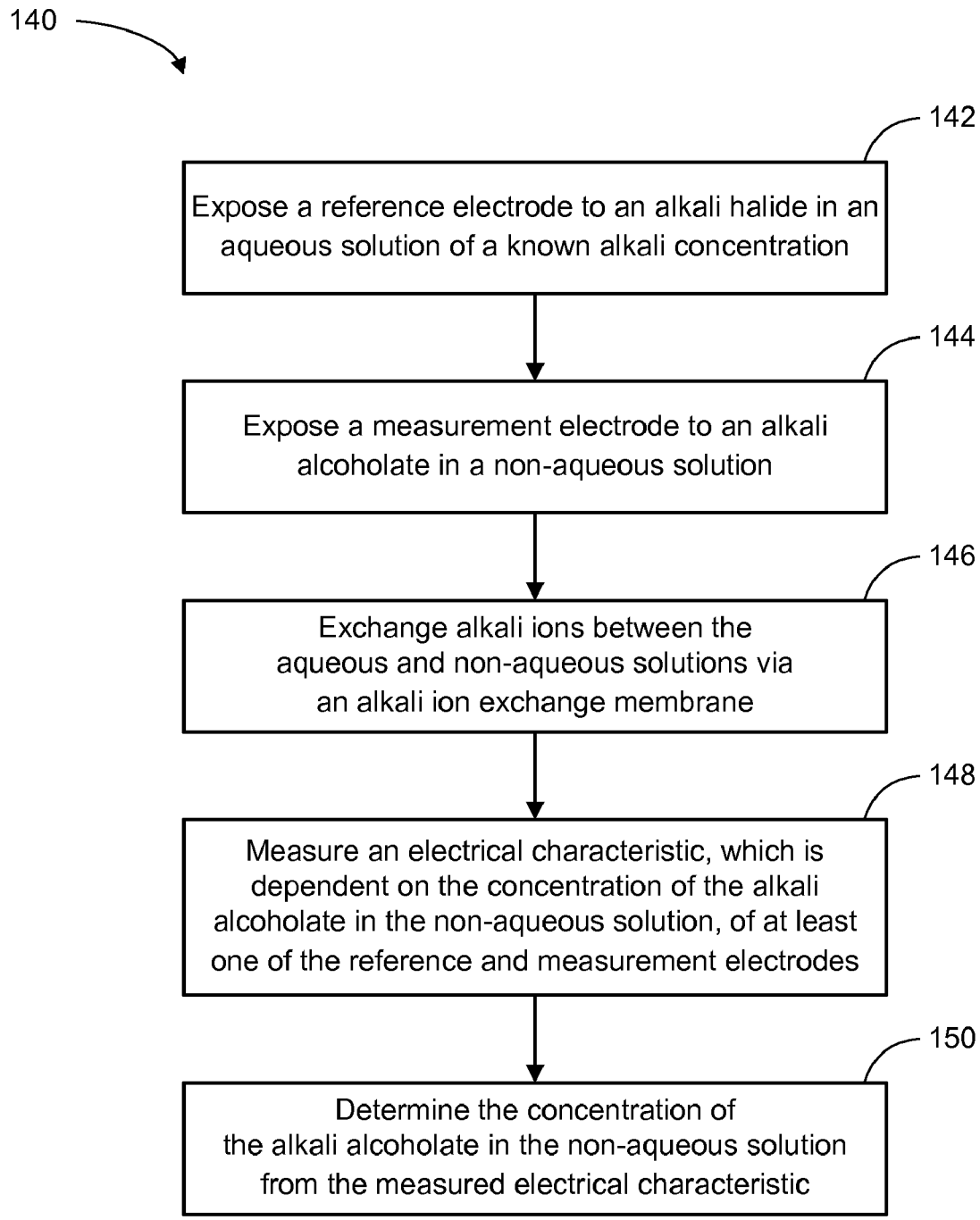
FIG. 4 depicts a flow chart diagram of one embodiment of a method for measuring a concentration of an alkali-based compound within a non-aqueous solution.

FIG. 4 depicts a flow chart diagram of one embodiment of a method 140 for measuring a concentration of an alkali-based compound (e.g., sodium methylate) within a non-aqueous solution 104. Although the method 140 is described in conjunction with the concentration sensor assembly 100 of FIG. 1A and the sensor system 120 of FIG. 2, other embodiments of the method 140 may be implemented with other sensor assemblies and/or sensor systems.

The illustrated method 140 includes exposing 142 the reference electrode 110 to an alkali halide (e.g., sodium chloride) in the aqueous solution 106 of a known alkali concentration. The measurement electrode 108 is exposed to an alkali alcoholate (e.g., sodium methylate) in the non-aqueous solution 104. As explained above, the solid alkali ion conducting membrane 102 (e.g., NaSICON) transports alkali ions 146 between the aqueous and non-aqueous solutions 106 and 104. In light of the solid alkali ion conducting between the aqueous and non-aqueous solutions 106 and 104, the test module 122 measures 148 an electrical characteristic (e.g., OCV) of at least one of the reference and measurement electrodes 110 and 108. The electrical characteristic is dependent on the concentration of the alkali alcoholate in the non-aqueous solution 104. The test module 122 determines 150 the concentration of the alkali alcoholate in the non-aqueous solution 104 based on the measured electrical characteristic. In one embodiment, the test module 122 invokes the evaluation module 126 to reference table data or an algorithm within the memory 132, as explained above. The depicted method 140 then ends.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Figure 5:
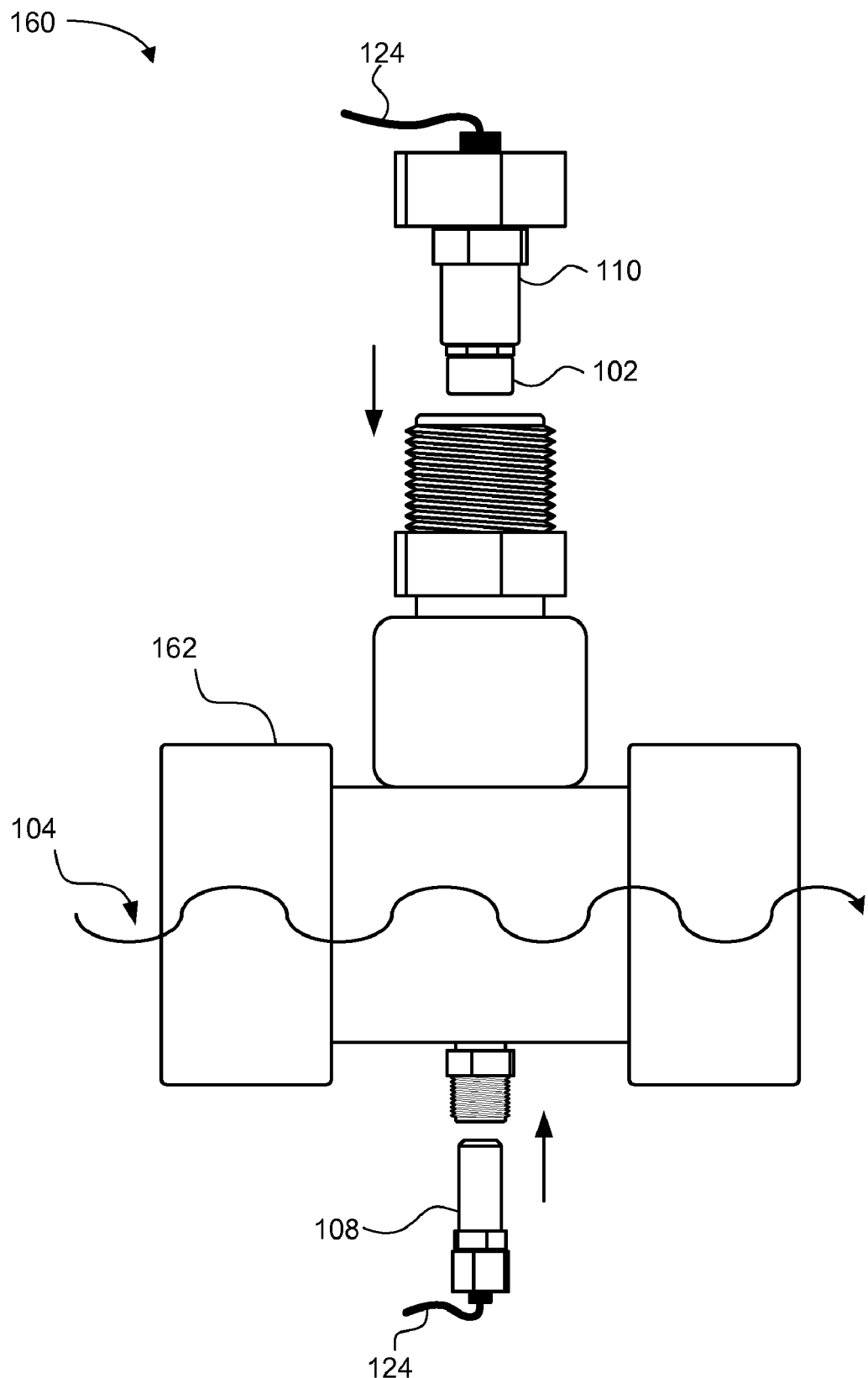
FIG. 5 depicts a schematic diagram of one embodiment of a measurement arrangement for the sensor assembly of FIG. 1A.

FIG. 5 depicts a schematic diagram of one embodiment of a measurement arrangement 160 for the sensor assembly 100 of FIG. 1A. In the illustrated embodiment, the measurement electrode 108 is inserted into a chamber 162 which contains the non-aqueous solution 104. In one example, the non-aqueous solution 104 flows through the chamber 162 as it enters or exits a holding tank (refer to FIG. 6). The reference electrode 110 and the solid alkali ion conducting membrane 102 are packaged together with a separate chamber of the aqueous solution 106. In one embodiment, the solid alkali ion conducting membrane 102 is exposed at the end of the chamber for the aqueous solution 106, so the solid alkali ion conducting membrane 102 is exposed one side to aqueous solution 106 and separately on the other side to the non-aqueous solution. As explained above, the electrical leads 124 from the measurement and reference electrodes 108 and 110 allow the test module 122 to determine a concentration of the non-aqueous solution 104 based on the voltage or amperage exhibited at the electrodes 108 and 110.

While the electrodes 108 and 110 are coaxially aligned, in the illustrated embodiment, other embodiments may include the electrodes 108 and 112 aligned in series with respect to the flow of the non-aqueous solution 104 within the chamber 162. For example, the measurement electrode 108 may be located upstream relative to the reference electrode 110. Other embodiments include other orientations of the measurement and reference electrode 108 and 110.

Figure 6:
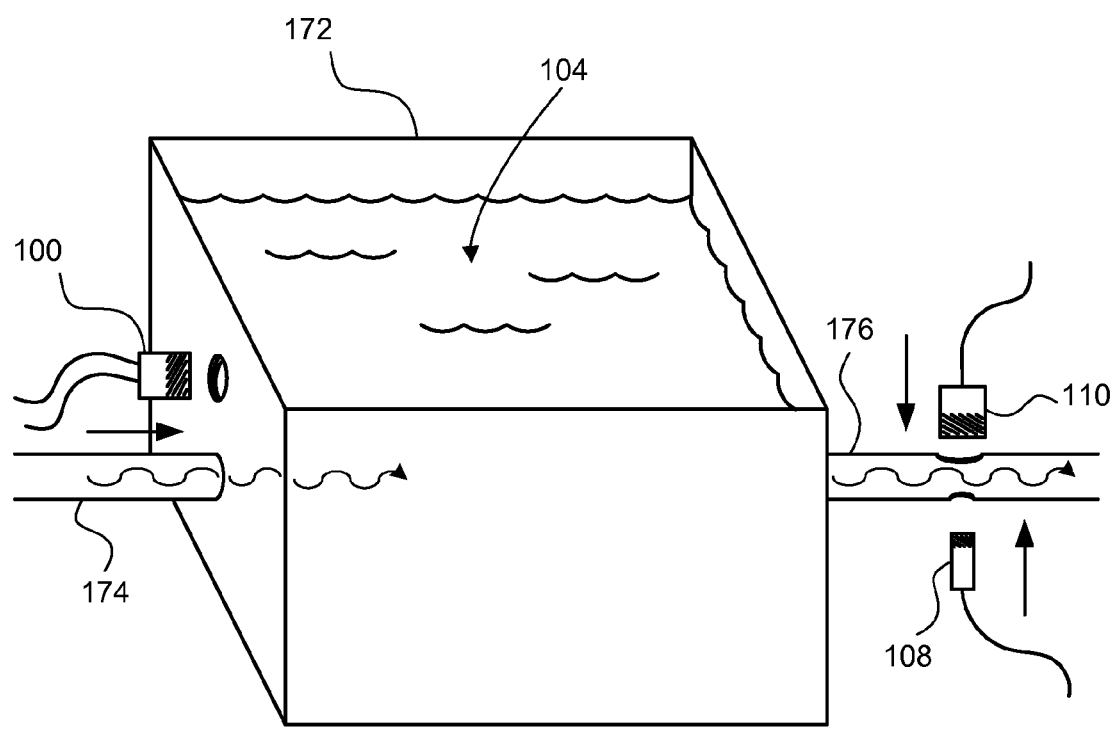
FIG. 6 depicts a schematic diagram of examples of sensor locations relative to a holding tank for the non-aqueous solution.

FIG. 6 depicts a schematic diagram of examples of sensor locations relative to a holding tank 172 for the non-aqueous solution 104. In the illustrated embodiment, the non-aqueous solution 104 flows into the holding tank 172 through an inlet channel 174. The non-aqueous solution 104 is held in the tank 172 and flows out of the tank 172 through an outlet channel 176. In the illustrated embodiment, the sensor assembly 100 of FIG. 1A is inserted directly into the structure of the holding tank 172 and exposed to the non-aqueous solution 104, while the aqueous solution is contained within the sensor assembly 100. Also, another sensor assembly 100, including separate measurement and reference electrodes 108 and 110 is located in the outlet channel 176. In one embodiment, the measurement and reference electrodes 108 and 110 located in the outlet channel 176 are mounted similar to the arrangement 160 shown in FIG. 5 and described above. Other embodiments may include one or more sensors mounted in other locations such as the inlet channel 174.

By mounting one or more sensors within the sodium methylate generation system, each sensor can monitor the concentration of the sodium methylate to indicate that proper concentration levels of the sodium methylate are maintained. In a further embodiment, at least one of the sensors can be used as a reference sensor. The reference sensor can be installed in a volume of solution having a known concentration of sodium methylate. For convenience in referring to the sensors, the sensor that is not the reference sensor may be referred to as a measurement sensor. By using a reference sensor in addition to a measurement sensor, the testing module 122 can monitor changes in the output signals of the reference signal in order to identify, for example, environmental changes that also affect the accuracy of the measurement sensor. For example, if temperature changes affect the output signal of the reference sensor, then similar modifications can be applied to the output signal of the measurement sensor to automatically compensate for the change in temperature.

Figure 7:
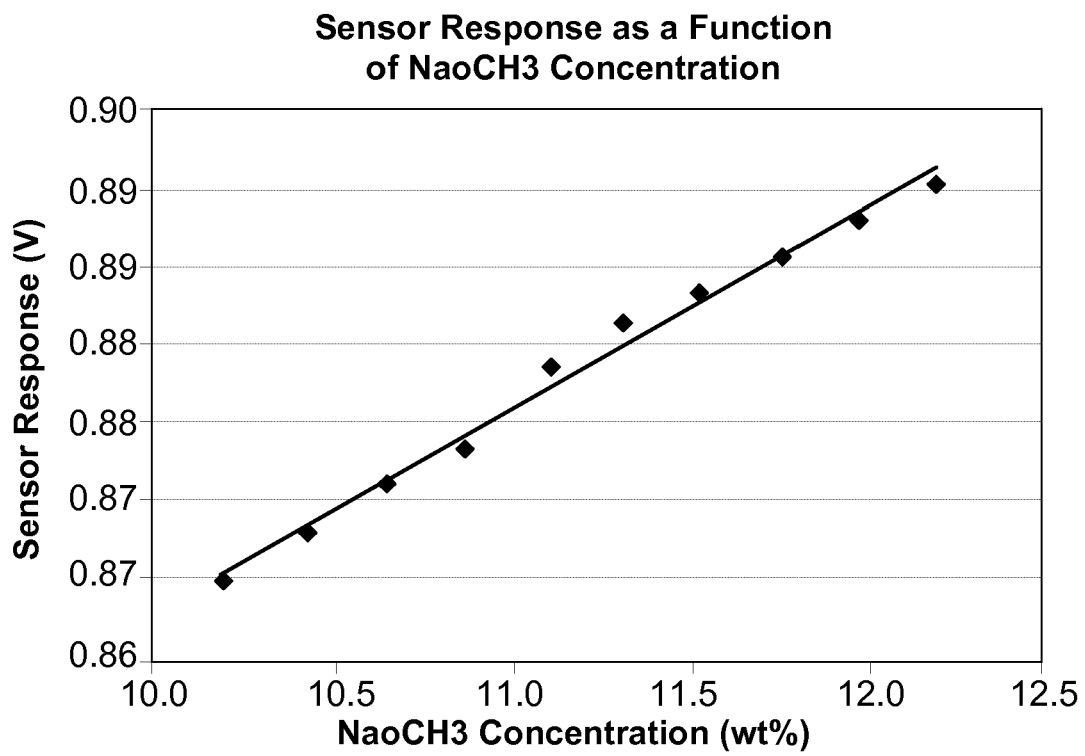
FIG. 7 depicts a graph of one example of a stable open circuit voltage of the sensor assembly of FIG. 5 as a function of continuously increasing sodium methylate concentration in methanol (concentration range=10.18% to 12.18%) during a flow through condition.

FIG. 7 depicts a graph of one example of a stable open circuit voltage of the sensor assembly of FIG. 5 as a function of continuously increasing sodium methylate concentration in methanol (concentration range=10.18% to 12.18%) during a flow through condition. In particular, FIG. 7 shows the performance of the sensor assembly 100 in FIG. 5 placed in an outlet channel (refer to FIG. 6) downstream of an electrolysis cell that continuously generates increasing concentration of sodium methylate. The data shows that the sodium methylate concentration in methanol increased from 10.18% to 12.18% during the test. The sensor 100 made measurements during a solution flow through condition (flow rate ~20 gallons per minute) in this case unlike the data in FIG. 3B that were measured in stagnant solutions. The data shows linearity ($R^2$=0.99) in the sensor OCV response with continuously increasing sodium methylate concentration in methanol.

Each of the data points in the graph represents a titration value to determine the exact concentration of sodium methylate in the stream.

Figure 8:
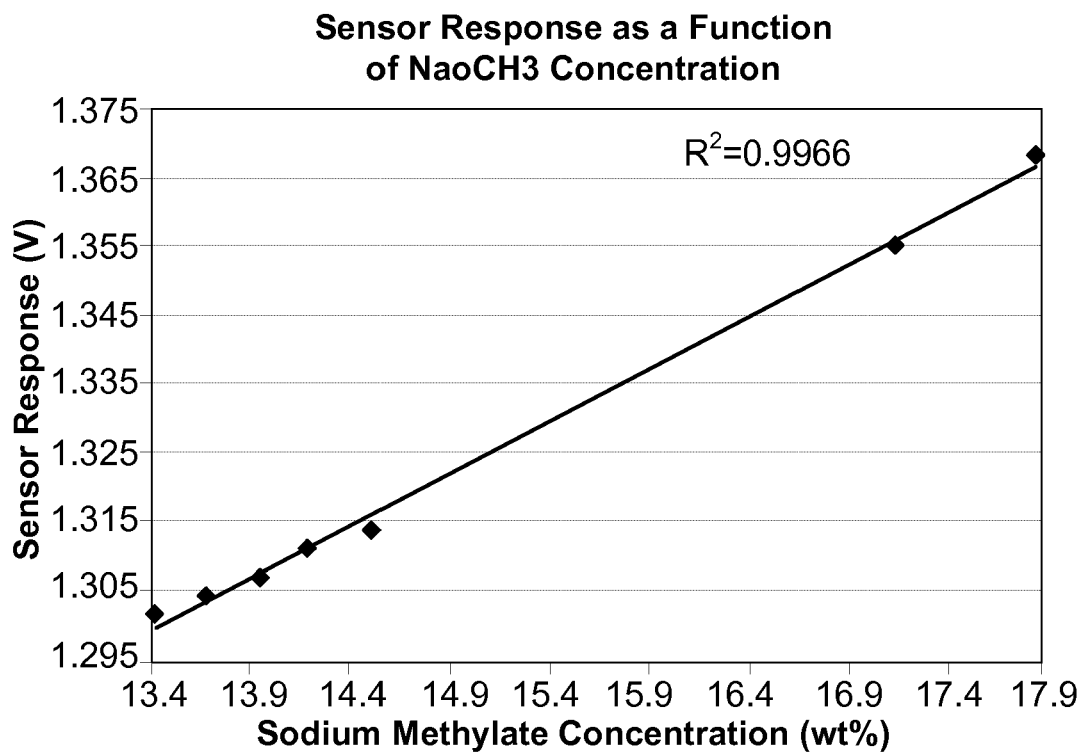
FIG. 8 depicts a graph of one example of a stable open circuit voltage of the sensor assembly of FIG. 5 as a function of continuously increasing sodium methylate concentration in methanol (concentration range=13.43% to 17.83%) during a flow through condition.

FIG. 8 depicts a graph of one example of a stable open circuit voltage of the sensor assembly 100 of FIG. 5 as a function of continuously increasing sodium methylate concentration in methanol (concentration range=13.43% to 17.83%) during a flow through condition. In particular, FIG. 8 shows the performance of the sensor assembly 100 in FIG. 5 placed in an outlet channel downstream of an electrolysis cell that continuously generates increasing concentration of sodium methylate. The sensor 100 made measurements during a solution flow through condition. The data shows that the sodium methylate concentration in methanol increased from 13.43% to 17.83% during the test. The data shows linearity ($R^2$=0.9966) in the sensor OCV response vs. sodium methylate concentration.

Figure 9:
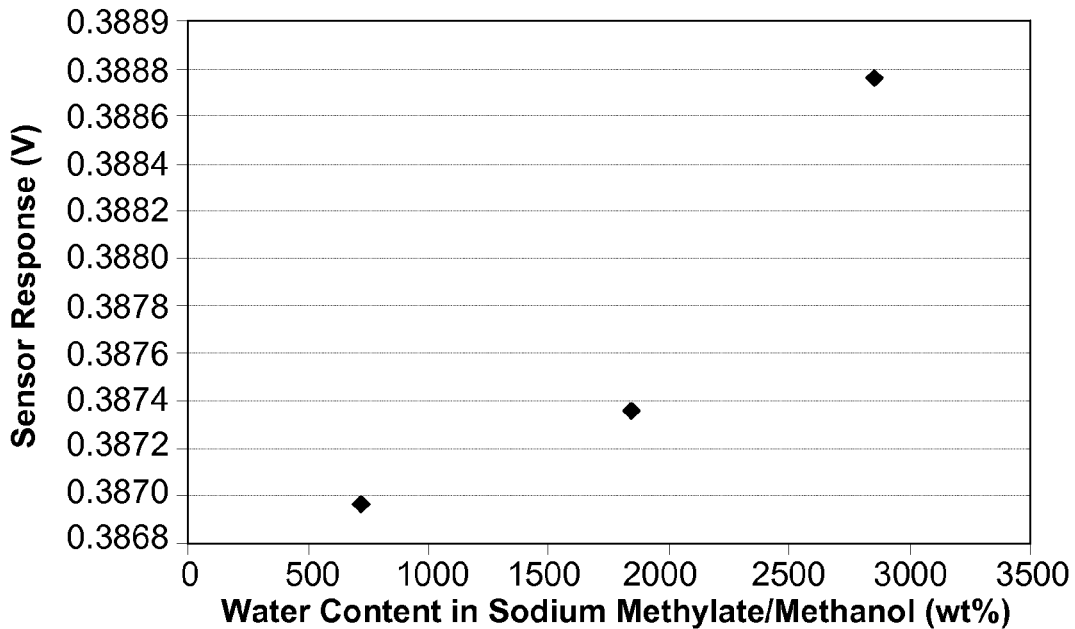
FIG. 9 depicts a graph of the effect of water content on sensor response in 11% sodium methylate in methanol.

FIG. 9 depicts a graph of the effect of water content on sensor response in 11% sodium methylate in methanol. Three separate samples of 11% sodium methylate with varying water contents of 720, 1840, 2860 PPM respectively (measured by Karl-Fischer Titration) were used to measure the sensor response. The data shows less than a 2 mV increase in sensor OCV response as the water content increased. This data demonstrates the minimal effect of water on the sensor response.

Figure 10:
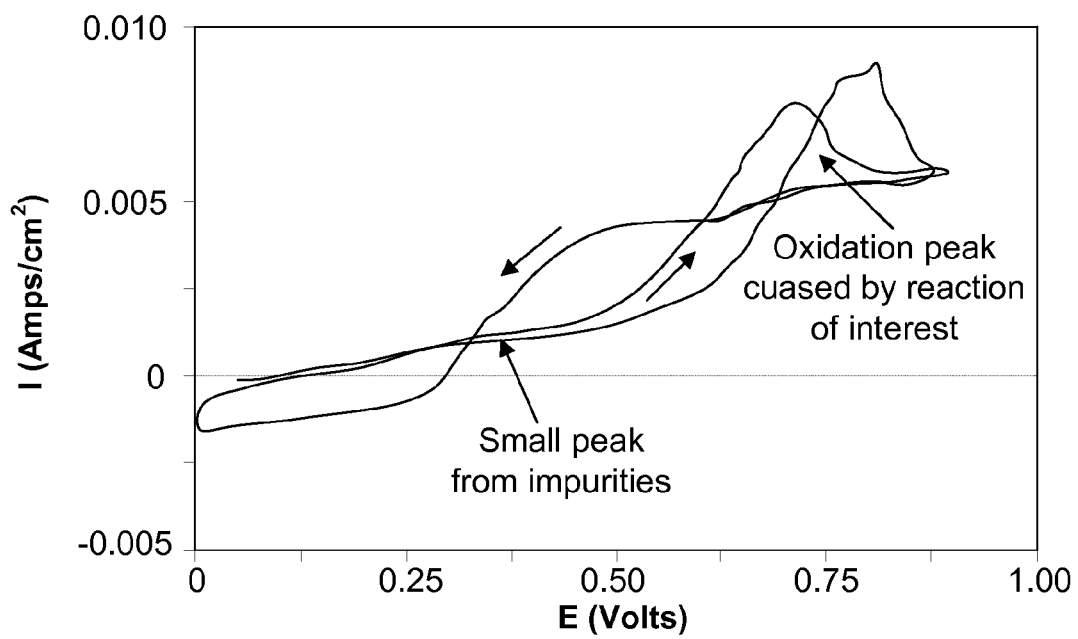
FIG. 10 depicts a cyclic voltammogram of a platinum measurement electrode in 20% sodium methylate in methanol.

FIG. 10 depicts a cyclic voltammogram of a platinum measurement electrode in 20% sodium methylate in methanol. The non-aqueous sensor response is expected to be non-Nernstean, and the potential value of the measurement electrode depends on a specific reaction at that electrode with sodium methylate under open circuit voltage conditions. The data shows an oxidation peak (positive current) due to oxidation of sodium methylate on methanol. This oxidation peak shifted to a lower potential after $1^{st}$ cycle and was reproduced during repeated cycling. The area under the oxidation peak is found to increase linearly with sodium methylate concentration.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for measuring a concentration of an alkali-based compound within a non-aqueous solution, the method comprising:
   exposing a reference electrode to an alkali halide in an aqueous solution of a known alkali concentration;
   exposing a measurement electrode to an alkali alcoholate in a non-aqueous solution;
   exchanging alkali ions between the aqueous and non-aqueous solutions via a solid alkali ion conducting membrane;
   measuring an electrical characteristic of at least one of the reference and measurement electrodes, wherein the electrical characteristic is dependent on the concentration of the alkali alcoholate in the non-aqueous solution; and
   determining the concentration of the alkali alcoholate in the non-aqueous solution from the measured electrical characteristic.

2. The method of claim 1, wherein measuring the electrical characteristic comprises measuring an open circuit voltage between the reference and measurement electrodes.

3. The method of claim 1, wherein measuring the electrical characteristic comprises measuring a current between the reference and measurement electrodes.

4. The method of claim 1, wherein exchanging the alkali ions between the aqueous and non-aqueous solution comprises exchanging the alkali ions through a solid alkali ion conducting membrane.

5. The method of claim 4, wherein the solid alkali ion conducting membrane is selected from a group consisting of:
   a sodium super ionic conductor (NaSICON) membrane;
   a sodium Nafion (Na-Nafion) membrane; and
   a sodium glass membrane.

6. The method of claim 1, wherein exposing the reference electrode to the alkali halide in the aqueous solution comprises exposing the reference electrode to a saturated solution of sodium chloride (NaCl).

7. The method of claim 6, wherein exposing the reference electrode to the alkali halide in the aqueous solution comprises exposing a silver/silver-chloride (Ag/AgCl) electrode to the saturated solution of sodium chloride (NaCl).

8. The method of claim 1, wherein exposing the measurement electrode to the alkali alcoholate in the non-aqueous solution comprises exposing the measurement electrode to sodium methylate ($NaOCH_3$) in methanol ($CH_3OH$).

9. The method of claim 8, wherein exposing the measurement electrode to the alkali alcoholate in the non-aqueous solution comprises exposing a platinum (Pt) electrode to the sodium methylate ($NaOCH_3$) in the methanol ($CH_3OH$).

* * * * *